US009597852B2

(12) United States Patent
Krumme

(10) Patent No.: US 9,597,852 B2
(45) Date of Patent: Mar. 21, 2017

(54) CHILDPROOF, HIGHLY INERT INDIVIDUAL PACKAGING

(71) Applicant: Markus Krumme, Allschwil (CH)

(72) Inventor: Markus Krumme, Allschwil (CH)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 14/803,039

(22) Filed: Jul. 18, 2015

(65) Prior Publication Data

US 2015/0321438 A1 Nov. 12, 2015

Related U.S. Application Data

(60) Division of application No. 13/136,746, filed on Aug. 9, 2011, now Pat. No. 9,145,248, which is a (Continued)

(30) Foreign Application Priority Data

Feb. 10, 2009 (DE) ........................ 10 2009 008 217

(51) Int. Cl.
*A61L 15/00* (2006.01)
*B65D 75/58* (2006.01)
(Continued)

(52) U.S. Cl.
CPC ................. *B31B 41/00* (2013.01); *A61J 1/03* (2013.01); *B65D 75/5805* (2013.01); *Y10T 29/4998* (2015.01)

(58) Field of Classification Search
CPC ............ B65D 75/5805; B65D 75/5827; B65D 75/5833; B65D 75/5894; A61J 1/00;
(Continued)

(56) References Cited

U.S. PATENT DOCUMENTS 5,511,665 A * 4/1996 Dressel .............. B65D 75/5827 206/469
5,613,779 A 3/1997 Niwa
(Continued)

FOREIGN PATENT DOCUMENTS

CA CA 2878330 A1 * 1/2014 ............. B65D 75/30
DE 600 12 842 T2 9/2005
(Continued)

OTHER PUBLICATIONS

English translation of the international Preliminary Report on Patentability for the corresponding international application—PCT/EP2010/000638 (5 pages).

*Primary Examiner* — Essama Omgba
(74) *Attorney, Agent, or Firm* — R. S. Lombard

(57) ABSTRACT

A method for producing childproof, highly inert individual dose packagings for transdermal therapeutic systems or film-like forms of administration in the form of a sealing edge bag that can be peeled back with a complete surrounding and continuous sealing surface, comprising two packaging elements, that are arranged on top of each other and form the upper side and the bottom side of a bag containing the product, wherein at least one layer of the packaging material elements is a metal layer and at least one packaging material element a film laminate with at least three-layer design; and the outer layer of the at least three-layer film laminate comprises at least one line-shaped weakening that is not touching the edge of the packaging on the upper and bottom side and the line-shaped weakening has a reduced resistance to tear for opening the packaging.

4 Claims, 1 Drawing Sheet

Related U.S. Application Data continuation-in-part of application No. PCT/EP2010/000638, filed on Feb. 3, 2010.

(51) Int. Cl.
*B31B 41/00* (2006.01)
*A61J 1/03* (2006.01)

(58) Field of Classification Search
CPC .. A61J 1/03; Y10T 29/4998; Y10T 29/49995; Y10T 29/49996
USPC ....... 206/440, 439, 441, 820, 828, 807, 484, 206/530, 532, 534.1, 484.2
See application file for complete search history.

(56) References Cited

U.S. PATENT DOCUMENTS

| | | | | |
|---|---|---|---|---|
| 6,074,097 | A | 6/2000 | Hayashi et al. | |
| 6,708,826 | B1 | 3/2004 | Ginsber et al. | |
| 7,607,834 | B2 * | 10/2009 | Alvater | B65D 75/5805 206/532 |
| 8,251,217 | B2 * | 8/2012 | Hemmerlin | B65D 75/5805 206/532 |
| 9,145,248 | B2 * | 9/2015 | Krumme | B65D 75/5805 |
| 2002/0008046 | A1 * | 1/2002 | Fuller | B26D 3/085 206/532 |
| 2005/0276525 | A1 * | 12/2005 | Hebert | B29C 59/007 383/203 |
| 2006/0023976 | A1 | 2/2006 | Alvater et al. | |
| 2007/0104917 | A1 | 5/2007 | Krug et al. | |
| 2008/0105582 | A1 | 5/2008 | Ludwig et al. | |
| 2008/0190809 | A1 * | 8/2008 | Simon | B65D 50/06 206/532 |
| 2010/0326877 | A1 * | 12/2010 | Hemmerlin | B65D 75/5805 206/532 |
| 2013/0199958 | A1 * | 8/2013 | Reichardt | B65D 75/30 206/484 |
| 2013/0341237 | A1 * | 12/2013 | Krumme | B65D 75/5805 206/530 |

FOREIGN PATENT DOCUMENTS

| | | | | | |
|---|---|---|---|---|---|
| DE | 10 2006 041 921 | A1 | | 3/2008 | |
| DE | CA 2751998 | A1 | * | 8/2010 | B65D 75/5805 |
| EP | 2105389 | A1 | * | 9/2009 | B65D 75/5805 |
| EP | 2354034 | A1 | * | 8/2011 | B65D 75/5805 |
| FR | WO 2010026142 | A1 | * | 3/2010 | B65D 75/5833 |
| GB | WO 2012084217 | A1 | * | 6/2012 | B65D 75/5833 |
| WO | WO 9312007 | A1 | * | 6/1993 | B65D 75/5805 |
| WO | WO 2010025899 | A1 | * | 3/2010 | B65D 75/42 |

* cited by examiner

CHILDPROOF, HIGHLY INERT INDIVIDUAL PACKAGING

CROSS-REFERENCE TO RELATED APPLICATION

This is a divisional application and claims the benefit of U.S. patent application Ser. No. 13/136,746 filed Aug. 9, 2011, now U.S. Pat. No. 9,145,248 B2 issued Sep. 29, 2015, which application is incorporated herein by reference in its entirety. The said U.S. patent application Ser. No. 13/136,746 is a continuation-in-part application of international application PCT/EP2010/000638 filed Feb. 3, 2010 and claiming the priority of German Application No. 10 2009 008 217.4 filed Feb. 10, 2009. The said international application PCT/EP/2010/000638 and the said German Application No. 10 2009 008 217.4 are both incorporated herein by reference in their entirety.

BACKGROUND OF THE INVENTION

The present invention relates to highly inert, single-dose packagings for forms of administration in film or foil form and transdermal therapeutic systems (TTSs), which are easy to open, but are nevertheless childproof.

The present invention also comprises a method for producing the single-dose packagings according to the invention which is distinguished by economical use of material.

Drug packagings have to perform a number of tasks. On the one hand, as a single dose, a packaging is intended for example to ensure that only a specific dose is ever taken at one time and that the taking of more than one dose is avoided.

On the other hand, the drug is also intended to be protected by the packaging from environmental influences such as light and moisture, which often lead to the active substance breaking down, and consequently to the medicament becoming unusable. Specifically in the case of containers that contain a number of dose units, here there is the problem that repeated opening of the container for the removal of a single dose adversely impairs the quality of the drug preparation, this impairment being all the greater the more sensitive the form of administration is with respect to mechanical and physical-chemical loads. Particularly drugs presented in film form impose particular requirements on the packaging, since the films are sensitive to physical-chemical influences (for example light, moisture or oxygen) on account of the large surface area and to mechanical loads on account of their structure.

In addition, the packagings are intended to prevent the drugs from being accessible to children, to take them unintentionally or administer the medication themselves.

On the one hand, a particular problem in the design of such secure drug packagings is that the packaging is intended to provide maximum security against unintentional self-medication, in particular by children driven by curiosity to open the packagings and confusing the medicaments, which are often colored and aromatized to mask the bad taste and/or smell of the active substances, for candy or other confectionery and taking them or applying the TTSs contained in the course of play.

On the other hand, however, the opening of the packaging is intended to be easy enough that adults, particularly including elderly persons and persons with motor difficulties, can open these packagings without any problems and that good compliance is ensured in the taking of the drugs.

As to be expected from the nature of the problem described above, a solution for achieving these objectives appears elusive, since children often approach the task of opening the packaging with great perseverance, ingenuity and intuition, while adult users often neglect the requisite study of the instructions or explanatory pictograms and unnecessarily take a knife or scissors to open the packaging, or else in the worst case fail to take the medication because of the difficulties in opening the packaging if these utensils do not happen to be to hand, with the result that patient compliance falls.

A further problem with single-dose packagings for forms of administration in film or foil form and transdermal therapeutic systems is that the surface area of the single dose is quite large in relation to the content of active substance in comparison with other forms of administration such as tablets or suppositories and cannot be reduced by bending and folding.

The size of the film consequently determines the size of the packaging. Furthermore, on account of the already discussed sensitivity of the films, the use of expensive high-barrier foils (high-barrier films), which can be subjected to mechanical loads and at most allow slight permeation of gases and moisture, is called for in order to ensure the necessary protection of the form of administration.

This gives rise to the disadvantage that both the upper side and the underside of the large-area form of administration has to be covered with a foil, which involves high expenditure on material and, as a result of the expensive foils, leads to high packaging costs, which may significantly increase the costs of the single dose and bring about an extremely unfavorable ratio of packaging costs to product costs. It should be mentioned in this respect that childproof packagings in particular often require additional expenditure on material in making them childproof.

The following proposals for easy-to-open, but childproof packagings are known from the prior art.

The laid-open patent application DE 10 2004 047 445 A1 discloses a non-reclosable packaging for harmful products, which has two packaging material elements arranged one lying on top of the other, a first area portion, at the peripheral edge or edges of which the two packaging material elements are releasably joined to one another, with at least one cavity that is enclosed on all sides for receiving the packaged product being formed between the two packaging material elements, and a second area portion, lying outside the first area portion or adjacent thereto, at the peripheral edge or edges of which the two packaging material elements are releasably joined to one another. At least one of the two packaging material elements is provided with at least one structure, which runs within the second area portion and makes it possible for the element or packaging material element or elements to be torn into.

The laid-open patent application US 2006/0023976 A1 describes peelable pouches for one or more doses of a drug in which two sheets of packaging material are peripherally sealed to one another, and which are provided in the region of the sealed peripheral edge with a surface structure which allows the pouch to be torn into and is crossed by a folding line. The peripheral edge of the pouch must be bent along the folding line in order that it can be torn into at the surface structure and opened.

The laid-open patent application DE 10 2006 041 921 A1 describes a childproof packaging for films containing active substances, which comprises a carrier layer and a top layer releasably joined to the latter and, in a paired arrangement, two opposing area regions which are separated from one another by a web and within which the top layer is not joined to the carrier layer, whereby two spaces that are separate from one another and enclosed on all sides are formed for receiving said films in pairs. Within said web there is a further area region, in which the carrier layer is not joined to the top layer, whereby a cavity that is enclosed on all sides is formed. Within the web there is at least one perforation line. The disadvantage of this approach is that a childproof packaging is only obtained for packaging paired films (forms of administration in film form). Although the opening of the childproof seal to expose one form of administration still leaves the other form of administration packed in a chemically sealed manner, the childproof seal is no longer present. To this extent, the use of a packaging according to DE 10 2006 041 921 A1 is only appropriate if the interval between taking the first single dose and taking the second single dose is not too great.

In the case of the foil packagings known from DE 10 2004 047 445 A1, US 2006/0023976 A1 and DE 10 2006 041 921 A1, the object of providing a childproof packaging which at the same time offers protection for the packaged product from chemical impairment is achieved by the use of a peelable pouch produced by heat sealing from two foils which respectively contain a thin aluminum layer. The foil packagings have a laterally applied cut, which however does not cut the side of the pouch itself. As a result, the pouch must be folded in the middle of the cut beyond an angle of 90° in order to produce a tearing notch in the side of the peripheral edge of the pouch. This exposes an opening aid for being gripped, with the aid of which the two foils of the pouch can be peeled from one another.

The solutions described above have in common that they are based on peelable foils, i.e. the laminate layer of the foil structure that is in contact with the product must be peelable and allow itself to be detached relatively easily from the layers lying thereover. These layers are virtually always polyethylene-based peeling layers or similar compositions that have a relatively weak sealing seam strength (are therefore peelable).

In addition, these foils have the disadvantage that they are often not inert with respect to active substance migration, which has the consequence that, in the course of the storage time, the active substances migrate into the packaging, and are consequently extracted from the drug. In terms of use, the sealing seam strength is usually also weakened by the sealed polymers being weakened by incorporation of other auxiliaries that are not weldable. As a side effect, these auxiliaries also cause reduced sealing seam impermeabilities for gases such as water vapor and oxygen, which may impair the storage stability of the packaging and lead to problems due to water absorption of hygroscopic products, as well as to increased degradation of oxygen-sensitive products.

Furthermore, the material consumption for producing the packaging is further increased by the opening of the packaging requiring the presence of non-sealed portions, which serve as a gripping aid for the "peeling", the minimum size of the gripping aids being limited by anatomical conditions.

The packaging of drugs/forms of administration in film or foil form consequently presents a particular challenge, since films and foils react sensitively to physical-chemical (for example light, moisture or oxygen) and mechanical loads.

Even if the packaging of individual forms of administration in film or foil form meets the requirements for the protection of the individually packaged product, it has the disadvantage that it is very expensive in practical implementation, because it requires high material use and the corresponding packagings can only be produced comparatively slowly.

The object of the present invention is to provide a childproof single-dose packaging for forms of administration in film or foil form and for transdermal therapeutic systems (TTSs) on the basis of sealed foils that ensures minimal foil consumption per single dose, is inert with respect to the packaged product, is easy to open and nevertheless has a maximum impermeability of the sealing seam.

It is also an object of the present invention to provide a method for producing single-dose packagings according to the present invention.

The object is achieved by a single-dose packaging according to the present invention and a corresponding method for producing the sealed single doses.

The object is achieved by a single-dose packaging according to the present invention and a corresponding method for producing the sealed single doses according to claim 1.

The single-dose packaging of the present invention is a tear-open sealed-edge pouch with a completely surrounding and continuous, therefore uninterrupted, non-peelable sealing area, the upper side and underside of the sealed-edge pouch being formed by two packaging material elements which are arranged one lying on top of the other and form a compartment for receiving the packaged product.

Since the present invention no longer requires the sealing seams to be peelable, highly inert sealing materials can be used, which in turn has favorable effects on the shelf life of the packaged product.

The sealing area preferably forms the outer limitations of the packaging, so that there is no gripping means at all for possible opening of the pouch by "peeling", i.e. opening of the pouch by releasing the sealing seams from one another or from the adjacent laminate layers. In this way, opening of the pouch by way of a weakened sealing seam that is not actually peelable is also prevented.

At least one layer of the packaging material elements is a metal layer, in order to ensure the required high impermeability of the single-dose packagings.

Furthermore, at least one packaging material element is a foil laminate having an at least three-layered structure, the outermost layer of which, facing away from the product, has a minimum resistance to tearing of 30 N, where N represents newtons, so that it is not possible for the packaging to be opened simply by tearing into it without any aid. On account of the high resistance to tearing of this first, at least three-ply packaging material layer, a more affordable foil laminate with a lower resistance to tearing can be used as the second packaging material element, in order to save costs.

In a preferred embodiment, however, the first and second packaging material elements have an identical structure.

In order to ensure unaided opening of the packaging, which cannot be opened manually on account of the tear-resistant outer layer of the laminate and the non-peelable sealing seams, the outermost layer of the at least three-layered foil laminate, which provides the resistance to tearing of the multi-layered laminate, has a linear weakening (line of weakness) with reduced resistance to tearing, lines of weakness that lie directly one on top of the another being provided on both sides of the single-dose packaging when identical, tear-resistant packaging material elements are used.

The line of weakness is preferably produced by the outer layer of the foil laminate, facing away from the packaged product, being removed or significantly reduced in thickness, so that the resistance to tearing is reduced.

In one embodiment, this reduction or removal of the outermost, tear-resistant layer of the foil laminates takes place by laser ablation or laser scoring (scoring by lasers), it being easy for this step to be included in the production process. However, other methods are also conceivable, such as specific mechanical removal or chemical etching or dissolving of the outer layer to present the line of weakness.

An alternative embodiment provides that the line of weakness is an interrupted line, i.e. that the tear-resistant layer has not been removed completely but small webs of tear-resistant material remain, but do not hinder the initial tearing and further tearing.

The advantage of this way of providing the line of weakness only in the outermost layer of the laminate is that the highly gas-impermeable metal layer is not damaged, and so maximum protection of the packaged product from moisture and oxygen is made possible.

Since, in preferred embodiments, the beginning of the line of weakness does not touch the periphery of the packaging, the packaging must first be bent in order to expose the beginning of the line of weakness along which the packaging can be torn open and which predetermines the tearing path.

While this two-stage working step can be readily accomplished by adults, it is not obvious to children, especially since only the uppermost layer of the foil laminate is weakened, but it is not the case, as known from the prior art, that the entire foil is weakened by an easily identifiable incision, which would also arouse the interest of a child.

A particularly preferred embodiment therefore provides that the outermost, tear-resistant layer should only be removed level with the identified bending region, which runs orthogonally in relation to the line of weakness, and that, in the further course of the line of weakness, the layer thickness should only be reduced to the extent that further tearing is possible but no longer initial tearing.

In a further embodiment, the resistance to tearing of the packaging material element is so great that further tearing is also only possible in the region of the line of weakness. In this way, tear propagation is prevented in regions of the packaging in which the mechanically sensitive product lies.

In a preferred embodiment, the line of weakness runs both through the sealing area and through the non-sealed product receiving region, the line of weakness preferably running parallel to the peripheral edge of the packaging and the line of weakness running through the non-sealed product receiving region at a distance of less than 5 mm, preferably less than 3 mm, particularly preferably less than 2 mm, and most preferably less than 1 mm, from the sealing area.

Furthermore, the line of weakness preferably extends over at least 50% of the length of the side of the packaging in which it is arranged, more preferably over at least 65%, still more preferably over at least 80% and particularly preferably over at least 90%, a maximum extent being restricted to 95%, since, according to the invention, the line of weakness does not touch the peripheral edge of the packaging.

A further embodiment provides that the packaging has two linear weakenings, which preferably run at right angles to one another and intersect at a point in a corner region of the packaging.

Furthermore, in a preferred form, the product receiving region has a protuberance reaching into the sealing area, the line of weakness running through the product receiving region in the region of the protuberance and the protuberance not running over the entire length of one side of the receiving region, but preferably over 95%-50% of the length of one side of the receiving region, more preferably over 85% to 55%, still more preferably over 75% to 60%, and particularly preferably over 66% of the length.

In one embodiment, the protuberance extends over two sides of the single-dose packaging, so that, with two lines of weakness, opening of the packaging can take place diagonally and the removal of the packaged product is made easier. In addition, these protuberances provide the necessary space for opening the packaging by separation at the tearing lines predetermined by the weakening, without destroying the product. The additional space is considered to be a safety zone, which prevents the product from being unwantedly affected and damaged in the course of the tearing, while the product is additionally secured in its position against slipping within the packaging by the closer limitation of the sealing peripheral edge in the remaining receiving region.

According to a further embodiment, the single-dose packaging has position restrictors for the product in the product receiving region, which are preferably produced by heat sealing. The position restrictors may in this case be formed as narrow joining webs between the upper and lower foil layers.

In order to identify the line of weakness and make the opening of the packaging easier, the line of weakness and/or the bending line may be identified, for example by a color marking or other usual means of identification.

The sealed-edge pouch of the present invention consists of two packaging material elements arranged one lying on top of the other, a first packaging material element and a second packaging material element.

The packaging material for producing the sealed-edge pouches is preferably a packaging material which has low permeation rates for gases and moisture.

For assuming the various functions that the packaging material has to perform, packaging materials having an at least three-layered structure are particularly well suited.

In the case of these packaging materials, in which the individual plies or layers of the packaging material are bonded together to form a composite, preferably in the form of a laminate, the individual layers of the packaging material assume one or more functions.

According to the present invention, the outermost layer of the packaging material element is distinguished by a high resistance to tearing, which cannot be destroyed manually without additional implements. However, an existing tear which has been produced at a predetermined, weakened point may be extended and tear propagation achieved, so that unaided manual further tearing is possible. A polyethylene terephthalate layer with a layer thickness of 12-25 μm is preferred as such a layer; however, other materials and layer thicknesses familiar to a person skilled in the art may also be used.

The outer layer can also preferably be printed on, so that for example product identifications and tearing-open suggestions can be provided.

In a preferred embodiment, the outer layer of the packaging material element is an oriented material, that is to say a monoaxially stretched material, the resistance to tearing of which is further increased in one direction, so that for example further tearing without a weakening of the outer layer is also not possible.

A second layer or, in the case of a three-layered structure, the middle layer consists of a metal foil, preferably aluminum, with a thickness of 9-25 μm. This metal layer provides the impermeability of the packaging with respect to moisture and air.

The inner layer is a sealable plastics layer, it not being possible for the sealing seam produced by this layer to be opened again. The joining of the laminates preferably takes place by heat sealing, but also by any other suitable sealing methods such as cold sealing, ultrasonic sealing, laser sealing or comparable foil welding methods known to a person skilled in the art, as long as a non-releasable sealing seam is obtained.

The sealing seams or sealing areas preferably have a width of 0.1 mm (millimeter) to 10 cm (centimeters), particularly preferably a width of 1 mm to 2 cm, and most particularly preferably a width of 2 mm to 8 mm, and they preferably extend over the entire length and width of the packaging material elements. At particularly exposed points, the sealing seam width may also be greater. In order to make the opening of the packaging additionally more difficult, at least one of the sealing seams may be made wider than the other sealing seams.

Coming into consideration as plastics are materials known to a person skilled in the art such as polyvinyl chloride (PVC), polyvinylidene chloride (PVDC), polypropylene (TP), polyethylene (PE), Barex® (BP Chemicals; a copolymer of acrylonitrile and butadiene), Surlyn®, Aclar™ (Honeywell; high-barrier foils of polychlorofluoroethylene [PCTFE]) and Topas®-COC (Ticona; cyclo-olefin copolymer foils), the layer thickness typically being 20-100 μm and plastics that are highly impermeable, behave inertly with respect to the active substance of the packaged form of administration and/or adsorb the latter only slightly being particularly suitable.

Surlyn® is an ionomer with high extensibility, which contains metal ions in the molecular chain and thereby exhibits crosslinkage.

A preferred Aclar® foil is Aclar® 33. Aclar® 33 is a copolymer which consists substantially of chlorotrifluoroethylene.

TOPAS®-COC are amorphous, transparent copolymers based on cyclic and linear olefins which are free from ionic constituents. A preferred TOPAS®-COC foil is produced from ethylene and norbornene.

A preferred Barex foil is a foil which is produced by graft copolymerization of 73-77 parts by weight of acrylonitrile and 23-27 parts by weight of methyl acrylate in the presence of 8-10 parts by weight of butadiene-acrylonitrile copolymer with a content of approximately 70% by weight of butadiene.

A particularly preferred high-barrier foil laminate for use as a packaging material element consists of a Barex® layer (20-40 μm), an aluminum foil (9-25 μm) and a PET layer (10-30 μm), where μm is micrometers.

The thickness of the multi-ply foil laminate preferably lies in the range of 35 to 300 μm, particularly preferably 50 to 200 μm.

The resistance to tearing of the packaging material is at least 30 N, preferably at least 40 N, and particularly preferably at least 50 N. The resistance to tearing of the packaging material preferably lies below 2000 N, particularly preferably below 200 N, and most particular preferably below 100 N, measured on the two packaging material elements joined to one another that form the packaging.

If different foil laminates are used as the first and second packaging material elements, the minimum tearability of the second foil laminate lies below that of the first foil laminate, it preferably being >30 N, particularly preferably >50 N.

The resistance to further tearing of the packaging material must not be too low, because then adequate protection of the packaged product can no longer be ensured and there is the risk of the packaging being unintentionally opened and/or the packaged product being damaged. This can be determined by simple tests. The resistance to further tearing of the packaging material is less than 20 N, preferably less than 5 N, particularly preferably less than 1 N, measured on the two packaging material elements joined to one another that form the packaging.

The resistance to tearing and the resistance to further tearing of the packaging material can be determined by means of known tensile testing machines using a sample holder for tear resistance tests (type no. 00740) (for example obtainable from FRANK Prüfgeräte GmbH, D-69488 Birkenau, Germany).

To make further tearing of the packaging material possible or easier, the resistance to tearing is a multiple of the resistance to further tearing. The ratio of resistance to tearing to resistance to further tearing preferably lies in the range of 20:1 to 500:1, particularly preferably in the range of 50:1 to 250:1, with respect to the resistance to tearing and the resistance to further tearing of the two packaging material elements joined to one another.

The resistance to tearing in the region of the line of weakness is less than 20 N, preferably less than 5 N, particularly preferably less than 1 N, measured on the two packaging material elements joined to one another to form the packaging.

BRIEF DESCRIPTION OF THE DRAWINGS

The single-dose packaging according to the invention is further explained below with reference to the figures. The figures serve here merely to illustrate the invention, without however the invention being restricted to what is shown.

DETAILED DESCRIPTION OF THE PARTICULAR EMBODIMENTS

Figure 1:
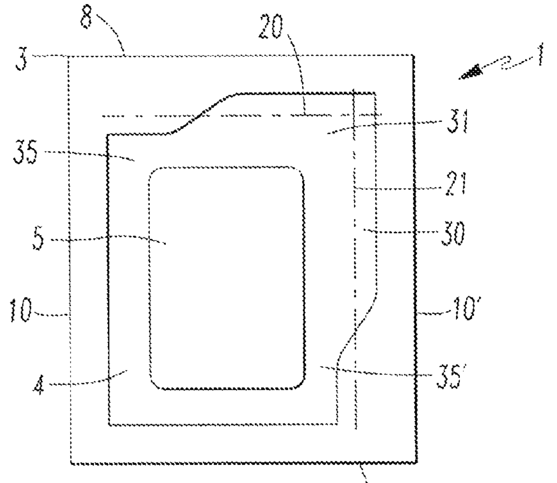
FIG. 1 shows a preferred embodiment of the single-dose packaging according to the invention in plan view with protuberances of the product receiving region and position restrictors over two sides of the packaging and two orthogonally running lines of weakness, which run over the region of the protuberances.
Figure 2:
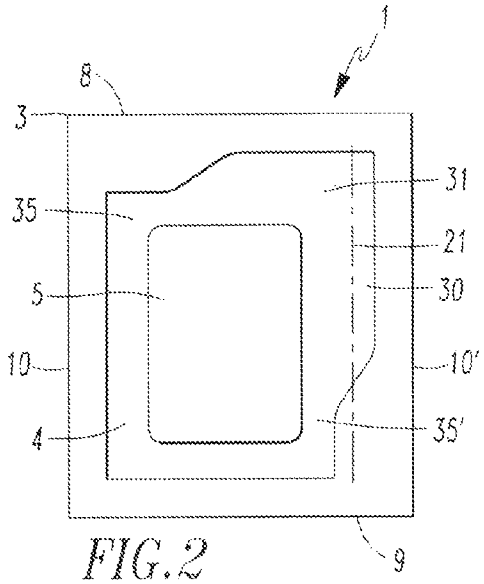
FIG. 2 shows a single-dose packaging as in FIG. 1, but only with one line of weakness along one side of the packaging.

The packaging (1) according to the invention is a sealed-edge pouch comprising two packaging material elements arranged one lying on top of the other, of which one packaging material element forms the top layer and the other packaging material element forms the bottom layer, between which the product (5), preferably a transdermal therapeutic system or a form of administration in film or foil form, is arranged. The two packaging material elements are in this case sealed to one another in such way that the product (5) is enclosed by a surrounding, continuous peripheral sealing edge (3), which is not peelable. This produces a product receiving region (4) which is closed on all sides and in which the product (5) is contained.

The sealed-edge pouch (1) has a front edge (8), a rear edge (9) and two preferably parallel running side edges (10, 10').

Furthermore, the sealed-edge pouch has lines of weakness (20, 21) with reduced resistance to tearing, along which the packaging material elements can be torn open.

In addition, the sealed-edge pouch in FIG. 1 has protuberances (31, 30) at the front edge (8) and at the side edge (10'), through which the tearing line defined by the lines of weakness runs, so that the product (5) is not damaged. Displacement of the product is prevented by the position restrictors (35, 35').

The packaging is made childproof by it only being possible to expose the lines of weakness for tearing open the packaging by overcoming a childproof seal. The seal consists in that the lines of weakness do not run as far as the peripheral edge and in that the otherwise tear-resistant material of the packaging material elements can only be torn open and the product removed after exposing the beginning of the line of weakness by bending the packaging over along a bending line, which may optionally be predetermined. On account of the resistance to tearing of the packaging material, it is not possible for the packaging to be torn into manually in other regions.

Since, for the weakening, merely the uppermost layer of the laminates is removed or reduced in only a very small region in relation to the surface area of the packaging, the resistance and impermeability of the packaging is impaired only minimally.

Figure 3:
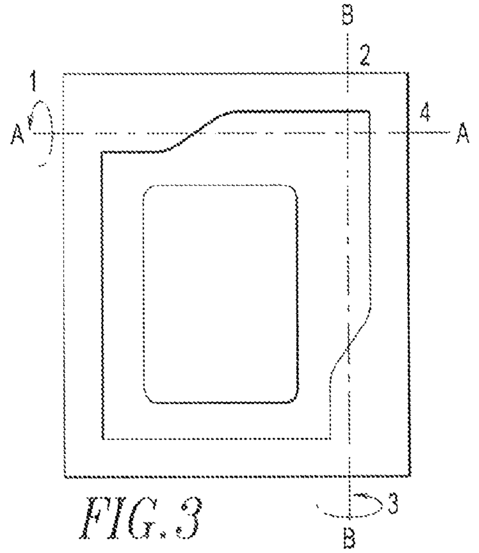
FIG. 3 shows the sequence of the bending and tearing operations for opening the single-dose packaging from FIG. 1.

According to the invention, the line of weakness for tearing into the packaging material should not touch the peripheral edge of the packaging, so that this structure only exposes the beginning of the region of weakness for tearing-in by folding the packaging along a line running through the structure, for example along the line A-A' (FIG. 3).

Said line of weakness, which makes it possible for the packaging element/s to be torn into, may be present in one of the two packaging material elements if, for example, the second packaging material element has a lower resistance to tearing or in both, the latter embodiment being preferred. In this case, the line of weakness for tearing into the packaging material is arranged congruently in the two packaging material elements.

The combination according to the invention of the packaging material and the configuration of the childproof seal makes it possible to design the packaging in such a way that opening is only possible by an ordered sequence of at least two steps:

(i) folding or bending over the packaging along a line, whereby the weakening structure becomes accessible for tearing-in;

(ii) tearing into the packaging at the then peripheral weakening structure and further tearing along the structure.

This handling involves considerable difficulties for children, particularly small children, especially since the line of weakness is not readily evident since there is only slight removal of material and no incision. For adults, however, it is possible without any problem and without the aid of implements. In a particularly preferred embodiment, the single-dose packaging is childproof in accordance with DIN EN 14375 and/or ASTM D3475-03a.

The present invention also relates to a method for producing a single-dose packaging for transdermal therapeutic systems or forms of administration in film form. This method is distinguished by the fact that it is particularly material-saving in comparison with the known methods.

Since there are no peelable seals and the packaging is torn directly along the line of weakness, no additional areas that expose gripping aids and the like, as are known from DE 10 2004 047 445 A1, are required for a childproof packaging.

The individual packagings lie directly against one another and additional material consumption, beyond the size of the packaged product, is dictated merely by the thickness of the sealing areas and, in certain embodiments, by the protuberances and position restrictors. There is likewise no scrap due to a complex exterior form. The production of the single-dose packagings according to the invention can consequently take place without any loss of packaging material.

The method for producing a single-dose packaging according to one of the preceding embodiments comprises the steps of:

providing a first packaging material sheet having an at least three-layered structure;

providing a second packaging material sheet;

positioning the packaged product on one of the two packaging material sheets;

laying the two packaging material sheets one on top of the other and joining them in such a way as to form for any packaged product a compartment for receiving the packaged product that is enclosed on all sides and at the peripheral edge or edges of which the two packaging material elements are unreleasably joined to one another;

providing at least one line of weakness by removing the uppermost, tear-resistant foil layer of the multi-layered foil laminate, the line of weakness running both through the sealing area and through the non-sealed product receiving region, but not touching the peripheral edge of the packaging;

individually separating the successive packaging units by a cut or a perforation along a line which runs transversely in relation to the sheet direction of the packaging material sheets in the region of the sealing area.

The sequence of the method steps that is indicated above is not obligatory; for example, the lines of weakness for tearing into the packaging material may also be provided only in a later step.

The unreleasable joining bond between the packaging material elements is preferably produced by heat sealing at temperatures in the range between 50° C. and 200° C., in particular 50° C. to 90° C. However, the unreleasable joining bond between the two packaging material sheets may also be produced by other heat sealing or cold sealing methods such as ultrasonic sealing, laser sealing or the like.

The packaging may, for example, be efficiently produced from strip stock by series production on rotary sealing machines.

In a preferred embodiment, the line of weakness is produced during production by laser ablation or laser scoring, the lines of weakness being provided congruently and directly opposite one another when tear-resistant foil laminates are used for the first and second packaging material elements.

Another embodiment provides that position restrictors are arranged in the product receiving region, preferably by heat sealing.

What is claimed is:

1. A method for producing successive packaging units where each packaging unit includes a single-dose packaging for transdermal therapeutic systems or forms of administration in foil form, in the form of a tear-open sealed-edge pouch including a product receiving region enclosing a packaged product, the tear-open sealed edge pouch also including a non-peelable completely surrounding and continuous sealing area or sealing seam, the tear-open sealed-edge pouch also comprising first and second packaging material elements, which are arranged with the first packaging material element lying on top of the second packaging material element and respectively forming the upper side and underside of the tear-open sealed-edge pouch which contains the product, at least one layer of the packaging material elements including a metal layer and at least one of the first and second packaging material elements being a foil laminate having an at least three-layered structure including an outer layer, a middle layer and an inner layer, and the outer layer of the at least three-layered foil laminate having a minimum resistance to tearing of 30 Newtons, the outer layer having at least one line of weakness, not touching the peripheral edge of the packaging, congruently on the upper side and underside of this outer layer and the at least one line of weakness having a reduced resistance to tearing for the opening of the packaging, the at least one line of weakness colinear with a bending line, the product receiving region has a protuberance reaching into the sealing area, the at least one line of weakness runs both through the sealing area and through the product receiving region in the protuberance, the protuberance not running the entire length of one side of the product receiving region, comprising the steps of:

providing the first packaging material element or sheet having an at least three-layered foil laminate structure with the outer, tear-resistant layer of the multi-layered foil laminate structure;

providing the second packaging material element or sheet;

positioning the packaged product on one of the two packaging material sheets;

laying the two packaging material sheets one on top of the other and joining them in such a way as to form for any packaged product the tear-open sealed-edge pouch for receiving the packaged product that is enclosed on all sides and at the peripheral edge or edges of which the two packaging material elements are unreleasably joined to one another;

providing the at least one line of weakness by removing either uniformly or intermittently the outer, tear-resistant layer of the multi-layered foil laminate, the at least one line of weakness running both through the sealing area and through the product receiving region in the protuberance, the protuberance not running the entire length of one side of the product receiving region;

individually separating successive packaging units by a cut or a perforation along a line which runs transversely in relation to the sheet direction of the packaging material sheets in the region of the sealing area.

2. The method as claimed in claim 1, characterized by in the step of providing at least one line of weakness, the at least one line of weakness is produced by laser ablation or laser scoring.

3. The method as claimed in 1, characterized by in the steps of providing the first and second packaging material elements or sheets they are structured in at least three layers and in the step for providing the at least one line of weakness in the first and second packaging material elements or sheets they are provided directly opposite one another.

4. The method as claimed in 1, characterized by in the step of joining the two packaging material sheets they are joined to one another by means of sealing seams of the sealing areas, using a sealing wax.

* * * * *